United States Patent [19]

Frickel et al.

[11] 4,329,352

[45] May 11, 1982

[54] PIPERIDINE DERIVATIVES OF 3-HYDROXY-THIOPHENE-2-CARBOXYLIC ACID ESTERS AND PHARMACEUTICAL FORMULATIONS CONTAINING THESE COMPOUNDS

[75] Inventors: Fritz-Frieder Frickel, Deidesheim; Gerda von Philipsborn, Weinheim; Claus D. Mueller, Viernheim; Dieter Lenke, Ludwigshafen, all of Fed. Rep. of Germany

[73] Assignee: BASF Aktiengesellschaft, Fed. Rep. of Germany

[21] Appl. No.: 212,631

[22] Filed: Dec. 3, 1980

[30] Foreign Application Priority Data

Dec. 13, 1979 [DE] Fed. Rep. of Germany ....... 2950064

[51] Int. Cl.$^3$ ................. A61K 31/445; C07D 417/12; A61K 31/38
[52] U.S. Cl. ...................................... 424/267; 546/213
[58] Field of Search ......................... 546/213; 424/267

[56] References Cited

U.S. PATENT DOCUMENTS 2,973,363  2/1961  Janssen ................................. 546/213
3,122,555  2/1964  Janssen ................................. 546/213
3,171,838  3/1965  Janssen ................................. 546/213

FOREIGN PATENT DOCUMENTS 1935558  1/1971  Fed. Rep. of Germany .
2242629  3/1973  Fed. Rep. of Germany .
2630152  1/1978  Fed. Rep. of Germany .
2720613  11/1978  Fed. Rep. of Germany .

*Primary Examiner*—Robert T. Bond
*Attorney, Agent, or Firm*—Keil & Witherspoon

[57] ABSTRACT

Substituted piperidino-alkyl ethers of 3-hydroxy-thiophene-2-carboxylic acid esters and their physiologically tolerated addition salts with acids, processes for their preparation, and pharmaceutical formulations which contain these compounds and which may be used in the treatment of cardiac arrhythmias.

4 Claims, No Drawings

PIPERIDINE DERIVATIVES OF 3-HYDROXY-THIOPHENE-2-CARBOXYLIC ACID ESTERS AND PHARMACEUTICAL FORMULATIONS CONTAINING THESE COMPOUNDS

The present invention relates to substituted piperidinoalkyl ethers of 3-hydroxy-thiophene-2-carboxylic acid esters and their physiologically tolerated addition salts with acids, processes for their preparation, and pharmaceutical formulations which contain these compounds and may be used in the treatment of cardiac arrhythmias.

German Laid-Open Application DOS No. 2,630,152 describes, for example, derivatives of 1-phenoxy-propan-2-ol which contain a 4-(pyrid-2-yl)-piperidin-4-ol radical and possess anti-arrhythmic properties. In addition, for example, phenoxypropanolamine and naphthoxypropanolamine derivatives which contain a 4-phenyl-piperidin-4-ol radical and which possess circulation-influencing properties, in particular hypotensive properties, are disclosed in German Laid-Open Application DOS No. 2,242,629, and piperazine derivatives of thiophene esters, having hypotensive properties, are also known. Those skilled in the art are however aware that the agents hitherto employed for dealing with cardiac arrhythmias are not always satisfactory and often have an insufficient therapeutic range.

We have found that compounds of the general formula I

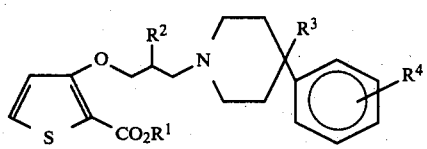

where
- $R^1$ is alkyl of 1 to 6 carbon atoms,
- $R^2$ is hydrogen or hydroxyl,
- $R^3$ is hydrogen, hydroxyl or carboalkoxy, where alkoxy is of 1 to 3 carbon atoms, and
- $R^4$ is hydrogen, halogen, trifluoromethyl or alkoxy of 1 to 3 carbon atoms, and the phenyl ring may possess 1 or 2 such $R^4$ substituents, and their physiologically tolerated addition salts with acids possess valuable pharmacological properties.

Compounds of the formula I, where $R^1$ is methyl or ethyl, $R^2$ is hydrogen or hydroxyl, $R^3$ is hydrogen, hydroxyl or carboethoxy and $R^4$ is hydrogen, fluorine, chlorine, bromine, trifluoromethyl or methoxy, and their physiologically tolerated addition salts with acids, are preferred.

Accordingly, examples of compounds according to the invention, of the formula I, in particular include 3-[2-hydroxy-3-(4-phenyl-4-hydroxy-piperidino)-propoxy]thiophene-2-carboxylic acid methyl ester, 3-[2-hydroxy-3-(4-phenyl-4-hydroxy-piperidino)-propoxy]-thiophene-2-carboxylic acid ethyl ester, 3-[2-hydroxy-3-(4-phenyl-4-hydroxy-piperidino)-propoxy]-thiophene-2-carboxylic acid butyl ester, 3-[3-(4-phenyl-4-hydroxy-piperidino)-propoxy]-thiophene-2-carboxylic acid methyl ester, 3-[3-(4-phenyl-4-hydroxy-piperidino)-propoxy]-thiophene-2-carboxylic acid ethyl ester, 3-[3-(4-phenyl-4-hydroxypiperidino)-propoxy]-thiophene-2-carboxylic acid propyl ester, 3-[3-(4-phenyl-4-hydroxy-piperidino)-propoxy]thiophene-2-carboxylic acid butyl ester, 3-[2-hydroxy-3-(4-(p-chlorophenyl)-4-hydroxy-piperidino)-propoxy]thiophene-2-carboxylic acid ethyl ester, 3-[2-hydroxy-3-(4-(p-chlorophenyl)-4-hydroxy-piperidino)-propoxy]thiophene-2-carboxylic acid methyl ester, 3-[2-hydroxy-3-(4-(p-chlorophenyl)-4-hydroxy-piperidino)-propoxy]thiophene-2-carboxylic acid butyl ester, 3-[2-hydroxy-3-(4-(p-fluorophenyl)-4-hydroxy-piperidino)-propoxy]thiophene-2-carboxylic acid methyl ester, 3-[2-hydroxy-3-(4-(p-fluorophenyl)-4-hydroxy-piperidino)-propoxy]-thiophene-2-carboxylic acid ethyl ester, 3-[2-hydroxy-3-(4-(m-trifluoromethylphenyl)-4-hydroxy-piperidino)-propoxy]-thiophene-2-carboxylic acid methyl ester, 3-[2-hydroxy-3-(4-phenyl-4-carboethoxy-piperidino)-propoxy]thiophene-2-carboxylic acid methyl ester, 3-[2-hydroxy-3-(4-phenyl-4-carboethoxy-piperidino)-propoxy]-thiophene-2-carboxylic acid butyl ester, 3-[2-hydroxy-3-(4-phenyl-piperidino)-propoxy]-thiophene-2-carboxylic acid methyl ester, 3-[2-hydroxy-3-(4-phenyl-piperidino)-propoxy]-thiophene-2-carboxylic acid ethyl ester, 3-[2-hydroxy-3-(4-phenyl-piperidino)-propoxy]-thiophene-2-carboxylic acid propyl ester and 3-[2-hydroxy-3-(4-phenyl-piperidino)-propoxy]-thiophene-2-carboxylic acid butyl ester.

The novel compounds are prepared by reacting a carboalkoxythiophene of the formula II

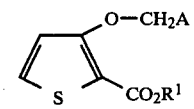

where $R^1$ has the meaning given for formula I and A is

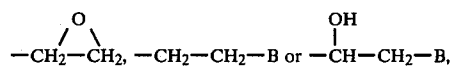

B being a nucleofugic leaving group, with a piperidine derivative of the general formula III

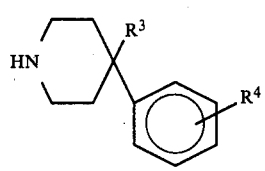

where $R^3$ and $R^4$ have the meanings given for formula I, in a conventional manner, advantageously in a solvent and in the presence or absence of an acid acceptor, and, if desired, converting the resulting compound into an addition salt with a physiologically tolerated acid.

The leaving group B is preferably halogen, especially chlorine, bromine or iodine. Further suitable nucleofugic leaving groups are aromatic and aliphatic sulfonic acid radicals, eg. the p-toluenesulfonic acid, p-bromobenzenesulfonic acid and methanesulfonic acid radicals.

The reaction is carried out at from 10° to 120° C., ie. at room temperature or above, advantageously at from 50° to 120° C. It may be carried out at atmospheric pressure or in a closed vessel under superatmospheric pressure, if appropriate with heating to the stated temperature range.

The starting compounds may be reacted without addition of a diluent or solvent. Advantageously, however, the reaction is carried out in the presence of an inert diluent or solvent, for example a lower alcohol of 1 to 4 carbon atoms, eg. methanol, ethanol or a propanol, preferably isopropanol or ethanol, a lower saturated dialkyl ether, dialkyl glycol ether or cyclic ether, eg. diethyl ether, 1,2-dimethoxyethane, tetrahydrofuran or dioxane, an aromatic hydrocarbon, such as benzene or an alkylbenzene, eg. toluene or xylene, a saturated aliphatic hydrocarbon, eg. hexane, heptane or octane, a lower aliphatic ketone, eg. acetone, methyl ethyl ketone or methyl isobutyl ketone, a dialkylformamide, eg. dimethylformamide or diethylformamide, or dimethylsulfoxide or water, or in mixtures of the above solvents.

Preferred solvents for the reaction of an epoxide of the formula (II), for example 1-(2-carbomethoxy-thienyl-3-oxy)-2,3-epoxypropane or 1-(2-carboethoxy-thienyl-3-oxy)-2,3-epoxypropane, with a piperidine derivative of the general formula (III) are lower alcohols, especially isopropanol, and the reaction is preferably carried out at from 50° to 120° C. under atmospheric pressure.

For the nucleophilic replacement of a radical B of a compound of the formula (II), for example of 1-(2-carbomethoxy-thienyl-3-oxy)-3-bromo-propane or of 1-(2-carbomethoxy-thienyl-3-oxy)-3-chloropropane, preferred solvents are lower aliphatic ketones, eg. acetone, diethyl ketone, methyl isopropyl ketone and methyl isobutyl ketone, cyclic saturated ethers, especially tetrahydrofuran and dioxane, or a dialkylformamide, eg. dimethylformamide, and preferred temperatures are 90°–180° C. The reaction may, if desired, be carried out in the presence of a catalytic amount of sodium iodide or potassium iodide.

A mixture of an epoxide and a halohydrin may also be used as the starting compound of the formula II, since such mixtures may under certain circumstances be formed when the starting compounds of the formula II are produced industrially.

In an advantageous embodiment of the nucleophilic replacement of the radical B by the piperidine derivative used, the reaction is carried out in the presence of a base as the acid acceptor. Preferred bases are alkali metal hydroxides, carbonates, bicarbonates and alcoholates, and tertiary organic amines, such as pyridine or a trialkylamine, eg. trimethylamine or triethylamine. Amongst the alkali metal compounds, those of sodium and potassium are particularly suitable. The base is employed in stoichiometric amount or in slight excess. It can also be advantageous to use an excess of the piperidine derivative (III) in the reaction, so as to serve simultaneously as an acid acceptor.

The time required for complete conversion depends on the reaction temperature and is in general from 2 to 15 hours. The reaction product can be isolated in a conventional manner, for example by filtration or by distilling the diluent or solvent from the reaction mixture. The compound obtained is purified in a conventional manner, for example by recrystallization from a solvent, conversion to an addition salt with an acid, or column chromatography.

The starting compounds of the formula II may be prepared in accordance with the processes described in German Laid-Open Application DOS No. 1,935,558, by alkylating 2-carbomethoxy-3-hydroxy-thiophene or 2-carboethoxy-3-hydroxy-thiophene with an epihalohydrin, an α,ω-dihalopropan-2-ol or an α,ω-dihalopropane. Suitable epihalohydrins include epichlorohydrin, epibromohydrin and epiiodohydrin, suitable α,ω-dihalo-propan-2-ols in particular include 1,3-dichloropropan-2-ol and 1,3-dibromo-propan-2-ol, and suitable α,ω-dihalopropanes in particular include 1,3-chlorobromopropane, 1,3-dichloropropane and 1,3-dibromopropane.

The reaction of the 2-carboalkoxy-3-hydroxythiophene, to prepare the starting compound of the formula II, is advantageously carried out at from 50° to 120° C., under atmospheric pressure or in a closed vessel under superatmospheric pressure. Advantageously, it is carried out in an inert diluent or solvent, for example a lower aliphatic ketone, eg. acetone, methyl ethyl ketone or methyl isobutyl ketone, a lower alcohol of 1 to 4 carbon atoms, eg. methanol, ethanol, propanol or butanol, a lower alkyl acetate, eg. methyl acetate, ethyl acetate or propyl acetate, a dialkylformamide, eg. dimethylformamide or diethylformamide, or dimethylsulfoxide, or using an excess of the alkylating agent as the diluent or solvent. Preferably, the reaction is carried out in the presence of a base as an acid acceptor. Suitable bases include alkali metal carbonates, bicarbonates, hydroxides and alcoholates, especially of sodium and potassium, basic oxides, eg. aluminum oxide and calcium oxide, and organic tertiary bases, such as pyridine or lower trialkylamines, eg. trimethylamine or triethylamine. The bases may be employed in catalytic amount or in stoichiometric amount or slight excess, relative to the alkylating agent used.

Preferably, the 2-carboalkoxy-3-hydroxy-thiophenes are reacted with epibromohydrin, 1,3-dibromopropan-2-ol or 1,3-dibromopropane in a lower aliphatic ketone, especially acetone or methyl isobutyl ketone, in the presence of not less than one mole equivalent (relative to alkylating agent) of a base, especially of potassium carbonate, at from 50° to 80° C.

Starting compounds of the formula II possessing an epoxy group and those possessing a halohydrin structure can be converted into one another by a simple acid-base reaction. Thus, a 1-(2-carboalkoxy-thienyl-3-oxy)-2,3-epoxypropane can be converted, by means of the appropriate hydrogen halide, into 1-(2-carboalkoxy-thienyl-3-oxy)-3-halo-isopropan-2-ol, the solvents or diluents used being conventional solvents, but preferably aliphatic or cyclic ethers, eg. diethyl ether, tetrahydrofuran or dioxane, or lower alcohols, eg. methanol, ethanol or propanol. Conversely, the 1-(2-carboalkoxy-thienyl-3-oxy)-3-halo-isopropan-2-ol compounds, especially 1-(2-carbomethoxy-thienyl-3-oxy)-3-chloro-isopropan-2-ol and 1-(2-carbomethoxy-thienyl-3-oxy)-3-bromo-isopropan-2-ol, can be converted to the 1-(2-carboalkoxy-thienyl-3-oxy)-2,3-epoxypropane by means of a base, such as an alkali metal hydroxide, carbonate, bicarbonate, alcoholate or hyride or an organic amine, such as pyridine, piperidine or a tertiary aliphatic amine, eg. trimethylamine or triethylamine. These reactions may be carried out at room temperature or may be accelerated, or completed, by heating, for example to 60°–120° C. The reaction may be carried out under atmospheric pressure or in a closed vessel under superatmospheric pressure, with or without heating. The starting materials for these interconversions may first be isolated or may be produced in situ and converted directly, without isolation or purification.

If desired, the resulting novel compounds are converted, in a conventional manner, to addition salts with physiologically tolerated acids. Examples of conventional physiologically tolerated acids are, amongst inorganic acids, hydrochloric acid, hydrobromic acid, phosphoric acid and sulfuric acid, and, amongst organic acids, oxalic acid, maleic acid, fumaric acid, lactic acid, tartaric acid, malic acid, citric acid, salicylic acid, adipic acid and benzoic acid; other examples may be found in Fort-schritte der Arzneimittelforschung, Birkhäuser-Verlag, Basel and Stuttgart, 10 (1966), 224–225.

The novel compounds of the formula I which possess a hydroxyl group on carbon atom 2 in the aliphatic side chain have a chirality center and are obtained as racemates which can be separated into the optically active antipodes by conventional methods, for example by forming diastereomeric salts with optically active auxiliary acids, such as dibenzoyltartaric acid, camphor-10-sulfonic acid, ditoluyltartaric acid or 3-bromocamphor-8-sulfonic acid.

The compounds according to the invention and their physiologically tolerated addition salts with acids possess a powerful anti-arrhythmic activity and may therefore be used, in particular, for the pharmacotherapy of cardiac arrhythmias.

To determine the anti-arrhythmic activity, the substance is administered orally to rats (Sprague Dawley, weight 200–250 g) 45 minutes before the start of narcosis. The animals are narcotized with 100 mg/kg of sodium thiobutabarbital administered intraperitone-ally. The arrhythmogenic substance is aconitine which is infused intravenously, at a dosage rate of 0.005 mg/kg×min, 60 minutes after administration of the novel substance. In the case of untreated animals (N=52), arrhythmias are noted in the electrocardiogram after 2.74±0.07 min, and the occurrence of these can be delayed by anti-arrhythmic agents, to an extent which depends on the dose.

The dose which prolongs the infusion duration by 50%, ie. the ED 50%, is determined from the linear relationship between log dose (mg/kg) of test substance and relative prolongation of aconitine infusion duration ($\Delta\%$).

For further characterization of the substance, the anti-arrhythmic effect of the maximum tolerated dose is determined from the decimal-geometric dosage progression (factor $\sqrt[3]{10}$) used in the experiments. In addition, the dose at which toxic symptoms (changes in the initial ECG, cyanosis or cramp) occur is determined. Moreover, the anti-arrhythmic activity of the compounds according to the invention is determined on isolated left atria of male guineapigs (Pirbright white, weight 350–450 g).

Atria suspended in an organ bath (volume 125 ml) containing carbogen-saturated Tyrode's solution (pH 7.4, 32° C.) are prestressed with 1.0 g and are driven by square wave pulses of 1 Hz base rhythm and double stimulation threshold values (rheo base: 0.2–1.4 V, chronaxia: 0.3–0.5 msec).

As a criterion of the anti-arrhythmic action, the frequency (in Hz) at which the atria are just still able to follow the sequence of pulses (the maximum driving rate) is determined by automatic continuous increase in frequency. The concentration which produces a 50% decrease in maximum driving rate, ie. the ED 50%, is calculated from the linear relationship between log concentration (mg/l) and relative decrease in maximum driving rate ($\Delta\%$).

Further, the concentration which produces a 25% decrease in amplitude, ie. the EC 25%, is determined, as a measure of the negatively inotropic effect, from the linear relationship between log concentration (mg/l) and relative change in contraction amplitude ($\Delta\%$).

The conventional anti-arrhythmic agent procainamide is used as the comparative substance.

The compound of Example 1 (cf. Table 1) has an anti-arrhythmic effect, on aconitine-induced arrhythmia in rats, which is 3 to 4 times greater than that of procainamide. A further advantage over procainamide is that the action on administration of the highest tolerated dose is greater. Procainamide prolongs the duration of aconitine infusion by a maximun of 135% whilst the compound of Example 1 produces a maximum increase of 296%.

The therapeutic range of the compound of Example 1, determined as the quotient of the toxic dose and the anti-arrhythmically effective dose (ED 50%), is 1.6 times greater than that of procainamide.

The anti-arrhythmic effect of the same novel compound on isolated guineapig atria (Table 2) is 69 times as great as that of procainamide. The difference between the anti-arrhythmic effect and the negatively inotropic effect—measured in terms of the quotient of EC 25% force of contraction decrease: EC 50% maximum driving rate—is substantially greater than for procainamide. Accordingly, the compound of Example 1 also has a greater therapeutic range as far as effects on guineapig atria are concerned.

TABLE 1

Anti-arrhythmic effect and toxicity in rats. Oral administration

| Substance | Anti-arrhythmic effect on aconitine-induced arrhythmia | | | | | Toxicity | |
|---|---|---|---|---|---|---|---|
| | Effective dose, mg/kg | | Maximum effect[3] | | | | |
| | ED 50%[1] | R.A.[2] | Dose | $\Delta$ %[4] | R.M.E.[5] | Dose[6] | Q[7] |
| Example 1 | 46.8 | 3.36 | 215 | 296 | 2.19 | 464 | 9.9 |
| Procainamide | 157 | 1.00 | 681 | 135 | 1.00 | 1,000 | 6.4 |

[1]Dose which prolongs the duration of aconitine infusion by 50%
[2]R.A. = relative activity. Procainamide = 1.00
[3]Effect of the maximum tolerated dose
[4]Prolongation of duration of aconitine infusion, $\Delta$ %
[5]R.M.E. = relative maximum effect. Procainamide = 1.00
[6]Dose whose administration produces the first toxic symptoms.
[7]$Q = \frac{\text{toxic dose}}{\text{ED 50\%}}$

TABLE 2

| | Effect on isolated guineapig auricles | | | | |
|---|---|---|---|---|---|
| | Maximum sequence frequency | | Force of contraction | | |
| Substance | EC 50%[1] | R.A.[2] | EC 25%[3] | R.A. | Q[4] |
| Example 1 | 1.47 | 68.7 | 3.80 | 14.8 | 2.6 |
| Procainamide | 101 | 1.00 | 56.4 | 1.00 | 0.56 |

[1]Concentration (mg/l) which produces a 50% decrease in the maximum sequence frequency
[2]R.A. = relative activity. Procainamide = 1.00
[3]Concentration (mg/l) which produces a 25% decrease in the force of contraction
[4]$A = \frac{\text{EC 25\% force of contraction}}{\text{EC 50\% decrease in sequence frequency}}$ Accordingly, the present invention also relates to therapeutic agents or formulations which contain a compound of the formula I, or a physiologically tolerated acid addition salt thereof, as the active compound, together with conventional carriers and diluents, and to the use of the novel compounds in the pharmacotherapy of cardiac arrhythmias.

The novel compounds may be used in the conventional solid or liquid pharmaceutical forms for administration, such as tablets, capsules, powders, granules, dragees or solutions. These are prepared in a conventional manner. For this purpose, the active compounds may be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous vehicles, wetting agents, dispersants, emulsifiers and/or preservatives (cf. L. G. Goodman and A. Gilman, The Pharmacological Basis of Therapeutics). The formulations obtained normally contain from 0.001 to 99% by weight of the active compound.

The preferred formulations are those suitable for oral administration. Examples of these are tablets, film tablets, dragees, capsules, pills, powders, solutions, suspensions or forms which have a depot effect. Parenteral formulations, such as injection solutions, may also be used. Further examples of suitable formulations include suppositories.

Appropriate tablets may be obtained, for example, by mixing the active compound with conventional auxiliaries, for example inert diluents, such as dextrose, sugar, sorbitol, mannitol, polyvinylpyrrolidone, calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetatephthalate or polyvinyl acetate. The tablets may also consist of a plurality of layers.

Accordingly, dragees may be prepared by coating cores, prepared in a similar manner to the tablets, with agents conventionally used in dragee coatings, for example collidone or shellac, gum arabic, talc, titanium dioxide or sugar. The dragee shell can also consist of several layers, in which the auxiliaries, mentioned above in connection with tablets, may be used.

Solutions or suspensions containing the novel active compounds may additionally contain flavorings, such as vanillin or orange extract. They may furthermore contain suspending agents, such as sodium carboxymethylcellulose, or preservatives, such as p-hydroxybenzoates. Capsules containing the active compounds may be prepared, for example, by mixing the latter with an inert carrier, such as lactose or sorbitol, and encapsulating the mixture in gelatin capsules. Suitable suppositories may be prepared, for example, by mixing the active compound with an appropriate carrier for this purpose, such as a neutral fat or polyethylene glycol or derivative thereof.

The dosage of the novel compounds depends on the age, condition and weight of the patient and on the route of administration. As a rule, the daily dose of active compound is from 5 to 100, preferably from 10 to 80, mg.

The Examples which follow illustrate the present invention.

PREPARATION OF STARTING COMPOUNDS

EXAMPLE I 1-(2-(Carbomethoxy-thienyl-3-oxy)-2,3-epoxypropane 800 g of 2-carbomethoxy-3-hydroxy-thiophene in 1.2 liters of epichlorohydrin are heated until the mixture refluxes, 480 g of a 50% strength aqueous sodium hydroxide solution are added in the course of one hour, and the azeotrope formed is separated in a water separator. After all the sodium hydroxide solution has been added, the mixture is refluxed for a further 15 minutes. It is then cooled, about 1 liter of epichlorohydrin is distilled off, and the residual reaction mixture is poured into water and extracted with methylene chloride. The extracts are dried over sodium sulfate and evaporated down, and the residue is distilled, giving 774 g of 1-(2-carbomethoxy-thienyl-3-oxy)-2,3-epoxypropane, boiling point 135°–142° C./0.2–0.3 mm Hg. This product solidifies slowly; melting point 74°–75° C.

$C_9H_{10}O_4S$ (214.2) Calculated: 50.5 C; 4.7 H; 29.9 O; 15.0 S. Found: 50.7 C; 4.7 H; 29.5 O; 14.8 S.

EXAMPLE II 1-(2-Carboethoxy-thienyl-3-oxy)-2,3-epoxypropane 75 g of 2-carboethoxy-3-hydroxy-thiophene, 50 ml of epibromohydrin and 100 g of dry potassium carbonate in 250 ml of acetone are refluxed for 10 hours. When it has cooled, the whole of the reaction mixture is poured into 3 liters of ice water and extracted with methylene chloride, and the combined extracts are washed with water and dried over sodium sulfate. The residue left after distilling off the solvent is subjected to fractional distillation, giving 55 g of 1-(2-carboethoxy-thienyl-3-oxy)-2,3-epoxypropane, of boiling point 147°–153° C./0.2 mm Hg.

$C_{11}H_{12}O_4S$ (228.2) Calculated: 57.9 C; 5.3 H; 14.0 S. Found: 57.6 C; 5.6 H; 13.8 S.

EXAMPLE III 1-(2-Carbomethoxy-thienyl-3-oxy)-3-chloro-propan-2-ol 4.0 g of 1-(2-carbomethoxy-thienyl-3-oxy)-2,3-epoxypropane are dissolved in a mixture of 20 ml of methanol and 15 ml of a 4 N solution of hydrogen chloride in ether. After the mixture has stood for one day, the volatile constituents are distilled off and the residue is chromatographed over silica gel, using methylene chloride. 2.1 g of 1-(2-carbomethoxythienyl-3-oxy)-3-chloro-propan-2-ol, which is pure according to NMR spectroscopy, are obtained.

$^1$H-NMR spectrum (CDCl$_3$, TMS as internal standard): =2.7 (d, J=5 Hz, 1H); 3.2 (d, J=5 Hz, 1H); 5.3 (s, OH); 5.8 (m, 3H); 6.3 (s, 3H); 6.3 (m, 2H).

EXAMPLE IV 1-(2-Carbomethoxy-thienyl-3-oxy)-3-chloropropane 79 g of 2-carboethoxy-3-hydroxy-thiophene, 118 g of 1,3-bromochloropropane and 104 g of dry potassium carbonate in 1 liter of acetone are refluxed for 8 hours. When the mixture has cooled, it is filtered and the filter residue is washed with acetone. The semicrystalline residue which remains is recrystallized from toluene, giving 99 g of 1-(2-carbomethoxy-thienyl-3-oxy)-3-chloropropane, of melting point 70°–71° C.

$C_9H_{11}ClO_3S$ (234.6) Calculated: 46.1 C; 4.7 H; 15.1 Cl; 13.7 S. Found: 46.4 C; 4.5 H; 15.0 Cl; 13.9 S.

PREPARATION OF COMPOUNDS ACCORDING TO THE INVENTION

EXAMPLE 1

100 g of 1-(2-carbomethoxy-thienyl-3-oxy)-2,3-epoxypropane and 82 g of 4-hydroxy-4-phenyl-piperidine in 400 ml of isopropanol are refluxed for 2 hours. The residue left after distilling off the solvent is recrystallized from ethanol, giving 145 g of 3-[2-hydroxy-3-(4-phenyl-4-hydroxy-piperidino)-propoxy]-thiophene-2- carboxylic acid methyl ester, of melting point 153°–154° C.

$C_{20}H_{25}NO_5S$ (391.2) Calculated: 61.4 C; 6.4 H; 3.6 N; 20.4 O; 8.2 S. Found: 61.4 C; 6.4 H; 3.5 N; 20.4 O; 8.2 S.

EXAMPLE 2

2.5 g of 1-(2-carbomethoxy-thienyl-3-oxy)-3-chloropropan-2-ol and 1.9 g of 4-hydroxy-4-phenylpiperidine in 50 ml of dioxane are heated for 10 hours at 120° C. in an autoclave. After distilling off the volatile constituents under reduced pressure, the very viscous crude product is partitioned between ether and 2 N sulfuric acid, and the aqueous phase is cautiously rendered alkaline with 4 N sodium hydroxide solution and is then extracted with ether. After drying the organic phase over magnesium sulfate, the solvent is removed and the residue is recrystallized twice from ethanol, as described in Example 1. 2.0 g of 3-[2-hydroxy-3-(4-phenyl-4-hydroxy-piperidino)-propoxy]-thiophene-2-carboxylic acid methyl ester of melting point 150°–152° C., identical with the material from Example 1, are obtained.

EXAMPLE 3

4.7 g of 1-(2-carbomethoxy-thienyl-3-oxy)-3-chloropropane, 3.5 g of 4-hydroxy-4-phenyl-piperidine and 2.7 g of sodium carbonate in 30 ml of N,N-dimethylformamide are refluxed for 20 hours. When the mixture has cooled, it is partitioned between water and methylene chloride and the residue which is left after evaporating the organic phase under reduced pressure is dissolved in a small amount of methanol. A solution of hydrogen chloride in ether is added dropwise thereto and the crystals which precipitate are filtered off, washed with ether and dried. 6.1 g of 3-[3-(4-phenyl-4-hydroxy-piperidino)-propoxy]-thiophene-2-carboxylic acid methyl ester hydrochloride hydrate, of melting point 122°–123° C., are obtained.

$C_{20}H_{28}ClO_5SN$ (430.9) Calculated: 55.7 C; 6.5 H; 18.6 O; 7.4 S, 3.3 N; 8.2 Cl. Found: 55.8 C; 6.5 H; 18.7 O; 7.6 S; 3.3 N.

The compounds shown in the Table which follows are obtained from 1-(2-carbomethoxy-thienyl-3-oxy)-2,3-epoxypropane or 1-(2-carboethoxy-thienyl-3-oxy)-2,3-epoxypropane and the corresponding piperidines, by the method described in Example 1.

TABLE 3

| Example No. | $R^1$ | $R^2$ | $R^3$ | $R^4$ | Salt form | Melting point, °C. | Analysis | | | | | |
|---|---|---|---|---|---|---|---|---|---|---|---|---|
| 4 | $C_2H_5$ | OH | OH | p-Cl | HCl | 174–175 | calc: 53.0 C | 5.7 H | 16.8 O | 2.9 N | 14.9 Cl | |
| | | | | | | | found: 52.9 C | 5.7 H | 16.9 O | 2.9 N | 15.1 Cl | |
| 5 | $CH_3$ | OH | OH | p-F | HCl | 154–155 | calc: 53.9 C | 5.7 H | | 3.1 N | 7.2 S | |
| | | | | | | | found: 53.9 C | 5.6 H | | 2.9 N | 7.2 S | |
| 6 | $CH_3$ | OH | OH | p-Cl | HCl | 192 (decomposition) | calc: 52.0 C | 5.5 H | | 3.0 N | 6.9 S | 15.3 Cl |
| | | | | | | | found: 52.4 C | 5.4 H | | 3.1 N | 7.0 S | 15.5 Cl |
| 7 | $CH_3$ | OH | OH | m-$CF_3$ | HCl | 154–156 | calc: 51.0 C | 4.9 H | 2.8 N | 6.5 S | 11.5 F | 7.1 Cl |
| | | | | | | | found: 50.0 C | 5.0 H | 2.7 N | 6.6 S | 11.5 F | 7.0 Cl |
| 8 | $C_2H_5$ | OH | OH | H | HCl | 136–138 | calc: 57.1 C | 6.4 H | 18.1 O | 3.2 N | 7.3 S | 8.0 Cl |
| | | | | | | | found: 57.0 C | 6.4 H | 18.0 O | 3.3 N | 7.2 S | 7.9 C |
| 9 | $CH_3$ | OH | $CO_2C_2H_5$ | H | HCl | 223–225 | calc: 57.1 C | 6.2 H | 19.8 O | 2.9 N | 6.6 S | 7.3 Cl |
| | | | | | | | found: 57.0 C | 6.1 H | 19.1 O | 3.1 N | 7.1 S | 6.9 Cl |
| 10 | $CH_3$ | OH | H | H | — | 115 | calc: 64.0 C | 6.7 H | | 3.7 N | 8.5 S | |
| | | | | | | | found: 64.0 C | 6.8 H | | 3.8 N | 8.6 S | |

| Example No. | Name |
|---|---|
| 4 | 3-[2-hydroxy-3-(4-(p-chlorophenyl)-4-hydroxy-piperidino)-propoxy]-thiophene-2-carboxylic acid ethyl ester |
| 5 | 3-[2-hydroxy-3-(4-(p-fluorophenyl)-4-hydroxy-piperidino)-propoxy]-thiophene-2-carboxylic acid methyl ester |
| 6 | 3-[2-hydroxy-3-(4-(p-chlorophenyl)-4-hydroxy-piperidino)-propoxy]-thiophene-2-carboxylic acid methyl ester |
| 7 | 3-[2-hydroxy-3-(4-(m-trifluoromethyl-phenyl)-4-hydroxy-piperidino)-propoxy]-thiophene-2-carboxylic acid methyl ester |
| 8 | 3-[2-hydroxy-3-(4-phenyl-4-hydroxy-piperidino)-propoxy]-thiophene-2-carboxylic acid ethyl ester |
| 9 | 3-[2-hydroxy-3-(4-phenyl-4-carboethoxy-piperidino)-propoxy]-thiophene-2-carboxylic acid methyl ester |
| 10 | 3-[2-hydroxy-3-(4-phenyl-piperidino)-propoxy]-thiophene-2-carboxylic acid methyl ester |

III. Examples of formulations

1. Tablets:

| | | |
|---|---|---|
| (a) | An active compound of the formula I | 5 mg |
| | Lactose | 200 mg |
| | Methylcellulose | 15 mg |
| | Corn starch | 50 mg |
| | Talc | 11 mg |
| | Magnesium stearate | 4 mg |
| (b) | An active compound of the formula I | 20 mg |
| | Lactose | 178 mg |
| | Avicel | 80 mg |
| | Polywachs 6000 | 20 mg |
| | Magnesium stearate | 2 mg |
| (c) | An active compound of the formula I | 50 mg |
| | Polyvinylpyrrolidone (mean molecular weight 25,000) | 170 mg |
| | Polyethylene glycol (mean molecular weight 4,000) | 14 mg |
| | Hydroxypropylmethylcellulose | 40 mg |
| | Talc | 4 mg |
| | Magnesium stearate | 2 mg |

The active compound is moistened with a 10% strength aqueous solution of the polyvinylpyrrolidone, forced through a sieve of 1.0 mm mesh width and dried at 50° C. The granules obtained are mixed with polyethylene glycol (mean molecular weight 4,000), hydroxypropylmethylcellulose, talc and magnesium stearate and the mixture is molded to form tablets each weighing 280 mg.

We claim:

1. A compound of the formula I

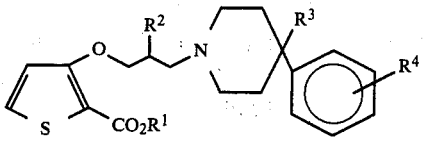

where
$R^1$ is alkyl of 1 to 6 carbon atoms,
$R^2$ is hydrogen or hydroxyl,
$R^3$ is hydrogen, hydroxyl or carboalkoxy, where alkoxy is of 1 to 3 carbon atoms, and
$R^4$ is hydrogen, halogen, trifluoromethyl or alkoxy of 1 to 3 carbon atoms, and the phenyl ring may possess 1 or 2 such $R^4$ substituents, and its physiologically tolerated addition salts with acids.

2. A compound of the formula I as claimed in claim 1, where $R^1$ is methyl or ethyl, $R^2$ is hydrogen or hydroxyl, $R^3$ is hydrogen, hydroxyl or carboethoxy and $R^4$ is hydrogen, fluorine, chlorine, bromine, trifluoromethyl or methoxy, and its physiologically tolerated addition salts with acids.

3. 3-[2-Hydroxy-3-(4-phenyl-4-hydroxy-piperidino)-propoxy]-thiophene-2-carboxylic acid methyl ester and its physiologically tolerated addition salts with acids.

4. A composition for treating cardiac arrhythmias which comprises an amount of a compound of formula I of claim 1 or a physiologically tolerated acid addition salt thereof effective for treating cardiac arrhythmias, and a pharmaceutically acceptable carrier or diluent.

* * * * *